United States Patent
Brighty et al.

(10) Patent No.: US 7,795,243 B2
(45) Date of Patent: Sep. 14, 2010

(54) PENEM PRODRUGS

(75) Inventors: Katherine E. Brighty, Groton, CT (US); Anthony Marfat, Mystic, CT (US); Dale G. McLeod, Ledyard, CT (US); John P. O'Donnell, North Stonington, CT (US)

(73) Assignee: Pfizer, Inc., New York, NY (US)

( * ) Notice: Subject to any disclaimer, the term of this patent is extended or adjusted under 35 U.S.C. 154(b) by 706 days.

(21) Appl. No.: 11/769,849

(22) Filed: Jun. 28, 2007

(65) Prior Publication Data

US 2008/0009474 A1    Jan. 10, 2008

Related U.S. Application Data

(60) Provisional application No. 60/911,587, filed on Apr. 13, 2007, provisional application No. 60/806,000, filed on Jun. 28, 2006.

(51) Int. Cl.
*C07D 499/887* (2006.01)
*A61K 31/431* (2006.01)
*A61P 31/04* (2006.01)

(52) U.S. Cl. .................................. 514/195; 540/310

(58) Field of Classification Search ................. 540/310; 514/195
See application file for complete search history.

(56) References Cited

U.S. PATENT DOCUMENTS

| | | | | |
|---|---|---|---|---|
| 4,619,924 A * | 10/1986 | Hamanaka | .................... | 514/195 |
| 4,870,170 A * | 9/1989 | Volkmann et al. | ............ | 540/310 |
| 4,952,577 A | 8/1990 | Alpegiani et al. | ............ | 514/192 |
| 5,013,729 A | 5/1991 | Volkmann | .................... | 514/195 |
| 5,326,884 A * | 7/1994 | Urban | .......................... | 549/66 |
| 5,506,225 A | 4/1996 | Iwata et al. | ................... | 514/195 |
| 5,703,068 A | 12/1997 | Iwata et al. | ................... | 514/195 |
| 2008/0125408 A1* | 5/2008 | Brighty et al. | ............... | 540/310 |
| 2009/0042853 A1* | 2/2009 | Brighty et al. | ......... | 514/210.05 |

FOREIGN PATENT DOCUMENTS

| WO | WO8808845 | 11/1988 |
|---|---|---|
| WO | WO9203444 | 3/1992 |
| WO | WO2004067532 | 12/2004 |

OTHER PUBLICATIONS

International Search Report for PCT/IB2007/001843 (Counterpart application).
Foulds, G., et al., "Pharmacokinetics of the penem CP-65,207 and it's separate stereoisomers in humans", Antimicrobial Agents & Chemotherapy, 1991, vol. 35 (4), pp. 665-671.
Foulds, G. et al., "Pharmacokinetics of the penem CP-65,207 and it's separate stereoisomers in humans [Erratum to document cited in CA115(3): 21555T]". Antimicrobial Agents & Chemotherapy, 1991, vol. 35 (8), p. 1695.
Gootz, Thomas, et al. "Pharmacokinetic studies in animals of a new parenteral penem CP-65,207 and it's oral prodrug ester", Journal of Antibiotics, 1990, vol. 43 (4), pp. 422-432.
Volkmann, et al., "2-Thioalkyl Penems: An Efficient Synthesis of Sulopenem . . . ", J. Org. Chem. 1992, vol. 57, pp. 4352-4361.
Wang, Y, et al. "Tebipenem pivoxil/tebipenem: carbapenem antibiotic.", Drugs of the Future, 2006, vol. 31(8), pp. 676-681.
Makoto, Tanaka et al, "Pharmacokinetics and safety of ascending single doses of DZ-2640, a new oral carbapenem antibiotic, administered to healthy Japanese students", Antimicrobial Agents and Chemotherapy, 2000, 44 (3), 578-582.
Kazuo, Umemura et al., "Safety and Pharmacokinetics of CS-834, a new oral carbapenem antibiotic, in healthy volunteers.", Antimicrobial Agents and Chemotherapy, 1997, vol. 41(12), pp. 2664-2669.
English Language Abstract of WO 2004/067532.
English Language Translation (Machine-Generated) of JP2006151814A (family member of WO 2004/067532).
English Language Translation (Machine-Generated) of JP2006151815A (family member of WO 2004/067532).
Volkmann, Robert, et al., "2-Thioalkyl Penems: An Efficient Synthesis of Sulopenem, a (5R,6S)-Hydroxyethyl)-2-[(cis-1-oxo-3-thiolanyl)thio]-2-penem Antibacterial", Journal Organic Chemistry, Dec. 18, 1992, pp. 4352-4361, vol. 57, No. 16.
Foulds, G., et al., "Pharmacokinetics of the Penem CP-65, 207 and Its Separate Stereoisomers in Humans", Antimicrobial Agents and Chemotherapy, Apr. 1991, pp. 665-671, vol. 35, No. 4.
Brass, E., "Pivalate-Generating Prodrugs and Carnitine Homeostasis in Man", Pharmacological Reviews, Dec. 2002, pp. 589-598, vol. 54, No. 4.

* cited by examiner

*Primary Examiner*—Mark L Berch
(74) *Attorney, Agent, or Firm*—Jennifer A. Kispert; J. Michael Dixon

(57) ABSTRACT

Orally bioavailable prodrugs of sulopenem, e.g.,

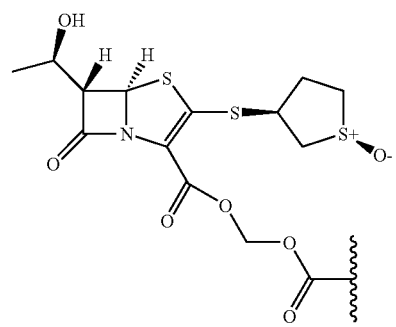

and solvates and hydrates thereof, preparation thereof, formulation thereof, and use to treat and prevent infection in mammals such as humans. This abstract is not limiting to the invention.

10 Claims, 4 Drawing Sheets

FIG. 5

| d value | 2-Theta ° | Intensity | Intensity % |
|---|---|---|---|
| 18.26027 | 4.835 | 3108 | 60.1 |
| 9.18278 | 9.624 | 4330 | 83.7 |
| 6.92727 | 12.768 | 430 | 8.3 |
| 6.11078 | 14.483 | 2759 | 53.3 |
| 5.30050 | 16.712 | 5174 | 100.0 |
| 5.18708 | 17.080 | 2396 | 46.3 |
| 4.86236 | 18.230 | 1683 | 32.5 |
| 4.75400 | 18.649 | 767 | 14.8 |
| 4.59001 | 19.322 | 1387 | 26.8 |
| 4.32314 | 20.527 | 1514 | 29.3 |
| 4.19978 | 21.137 | 860 | 16.6 |
| 3.99389 | 22.240 | 577 | 11.2 |
| 3.94639 | 22.511 | 907 | 17.5 |
| 3.75759 | 23.658 | 3098 | 59.9 |
| 3.45923 | 25.732 | 1421 | 27.5 |
| 3.25936 | 27.340 | 758 | 14.7 |
| 3.20146 | 27.844 | 426 | 8.2 |
| 3.03698 | 29.385 | 503 | 9.7 |
| 3.01040 | 29.651 | 412 | 8.0 |
| 2.92866 | 30.498 | 401 | 7.8 |
| 2.88994 | 30.917 | 348 | 6.7 |
| 2.76299 | 32.375 | 449 | 8.7 |
| 2.64868 | 33.814 | 316 | 6.1 |
| 2.57969 | 34.746 | 442 | 8.5 |
| 2.53966 | 35.312 | 244 | 4.7 |
| 2.51050 | 35.736 | 255 | 4.9 |
| 2.28153 | 39.463 | 350 | 6.8 |

FIG. 6

| d value | 2-Theta ° | Intensity | Intensity % |
|---|---|---|---|
| 17.82492 | 4.953 | 1838 | 71.5 |
| 9.26907 | 9.534 | 667 | 26.0 |
| 8.85757 | 9.978 | 1917 | 74.6 |
| 6.84872 | 12.916 | 314 | 12.2 |
| 5.88550 | 15.041 | 2569 | 100.0 |
| 5.44080 | 16.278 | 655 | 25.5 |
| 5.18066 | 17.101 | 1135 | 44.2 |
| 4.87518 | 18.182 | 673 | 26.2 |
| 4.71380 | 18.810 | 988 | 38.5 |
| 4.09211 | 21.700 | 552 | 21.5 |
| 4.00937 | 22.153 | 399 | 15.5 |
| 3.76619 | 23.603 | 226 | 8.8 |
| 3.55534 | 25.025 | 1025 | 39.9 |
| 3.35547 | 26.542 | 162 | 6.3 |
| 3.20310 | 27.830 | 135 | 5.3 |
| 3.08747 | 28.894 | 184 | 7.2 |
| 2.94178 | 30.359 | 184 | 7.2 |
| 2.83532 | 31.528 | 220 | 8.6 |
| 2.46449 | 36.426 | 170 | 6.6 |
| 2.36407 | 38.031 | 125 | 4.9 |
| 2.28144 | 39.465 | 116 | 4.5 |

PENEM PRODRUGS

FIELD AND BACKGROUND

The present invention relates to antiinfectives, antibiotics, oral antibiotics, and prodrugs, in particular, sulopenem prodrugs, their preparation, and use.

U.S. Pat. No. 5,013,729 describes sulopenem, which is a broad-spectrum antibiotic that can be named as (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylic acid. See also *J. Org. Chem.*, 57, 4352-61 (1992).

Other penems and prodrugs are discussed in, e.g., U.S. Pat. No. 4,952,577; U.S. Pat. No. 5,506,225; WO1992/003444; and WO2004/067532.

Various preclinical and clinical studies have been conducted with sulopenem and certain prodrugs thereof. Sulopenem itself is not appreciably orally bioavailable. U.S. Pat. No. 5,013,729 also discusses sulopenem prodrugs, including the pivaloyloxymethyl prodrug of sulopenem (sulopenem POM ester). When given orally as a mixture of two stereoisomers, the POM ester was shown to be orally bioavailable in humans. See Foulds et al., *Antimicrobial Agents and Chemotherapy*, pp. 665-671 (April 1991). However, POM ester prodrugs are associated with tissue carnitine depletion following hydrolysis and release of pivalic acid or trimethyl acetic acid. See Brass, *Pharmacological Reviews*, 54, 589-598 (2002).

SUMMARY

The present invention addresses a desire for new sulopenem prodrugs that combine one or more of: high oral exposure or bioavailability, a lack of propensity to deplete tissue carnitine, physicochemical properties, such as crystallinity, melting point, aqueous solubility, and permeability, which are favorably suited to practical pharmaceutical formulation and use.

In some aspects, the present invention includes the compounds of Formula I (at multiple locations later in the specification this same compound is referred to as Compound 1. The reader should treat the term "Formula I" and "Compound 1" as interchangeable):

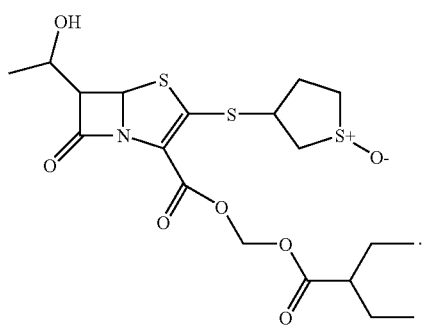

I

In other aspects, the present invention includes the compounds of Formula II (at multiple locations later in the specification this same compound is referred to as Compound 2. The reader should treat the term "Formula II" and "Compound 2" as interchangeable):

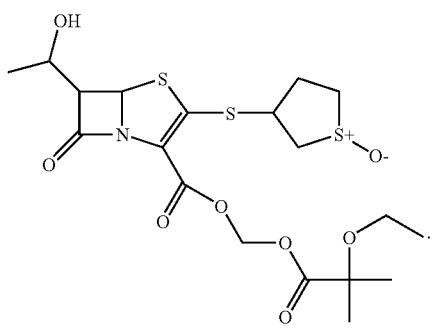

II

The invention further includes formulations and use of the compounds to treat or prevent bacterial infection.

BRIEF DESCRIPTION OF THE DRAWINGS

FIG. 5 is a table containing x-ray powder diffraction data for (2-ethyl-1-oxobutoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate (Compound 1).

FIG. 6 is a table containing x-ray powder diffraction data for (2-ethoxy-2-methyl-1-oxopropoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate (Compound 2).

DETAILED DESCRIPTION

Compounds

Figure 1:
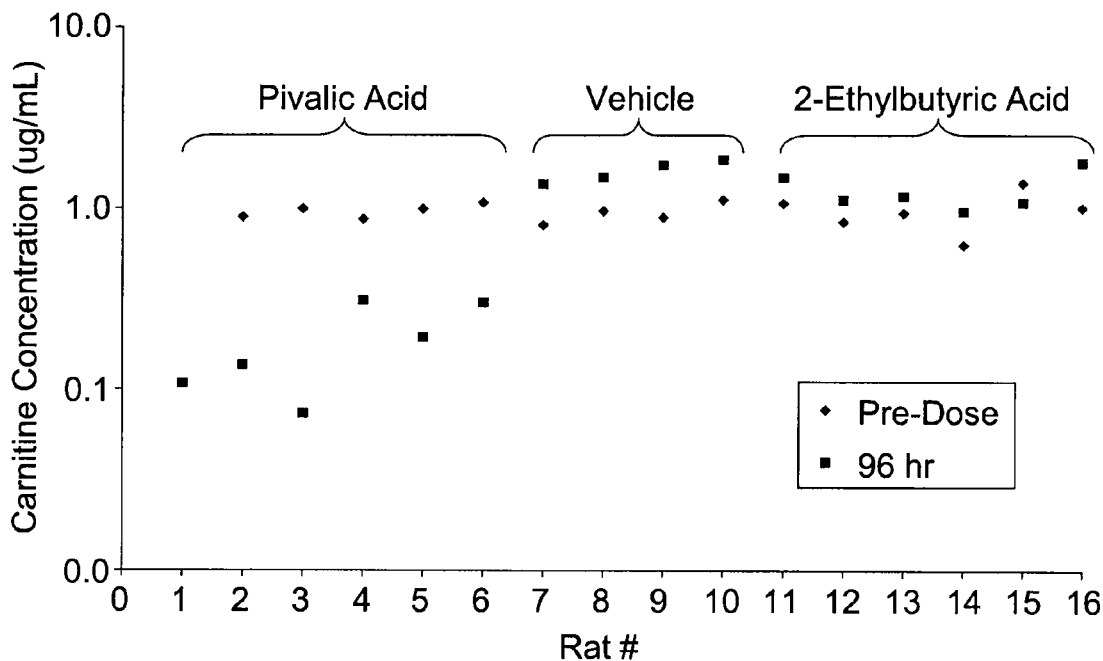
FIG. 1 shows the amount of plasma carnitine in animals receiving 200 mg/kg BID over a course of 4 days of treatment with either pivalic acid, vehicle control or 2-ethylbutyric acid.

The present invention includes the prodrug compounds of Formulas I and II, as shown and described above. All stereoisomers and mixtures thereof are contemplated and included, as indicated by the drawings above that allow for and embrace both the R and the S configurations at stereocenters.

A preferred configuration of the compounds of Formulas I and II is:

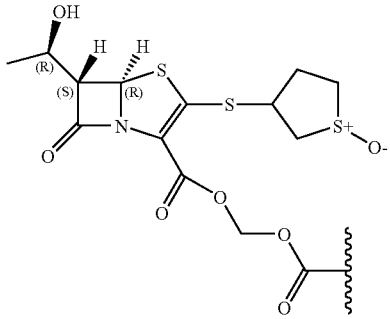

In particular, the oxothiolanyl moiety is preferably configured 1R, 3S, as shown below.

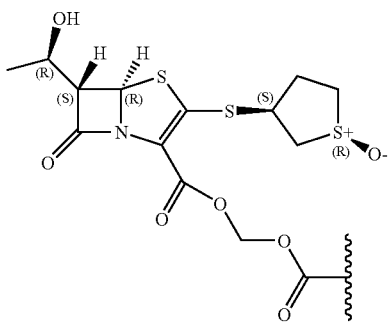

For example, there is provided: (2-Ethyl-1-oxobutoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate (Compound 1 herein), which is drawn below:

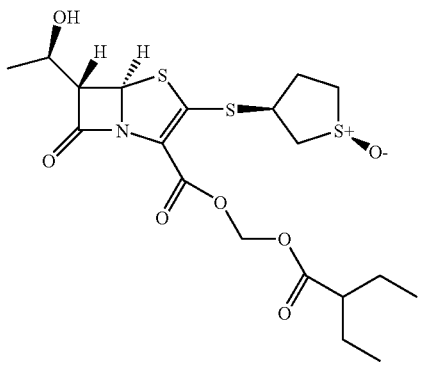

Another example provides: (2-Ethoxy-2-methyl-1-oxopropoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate (Compound 2 herein), which is drawn below:

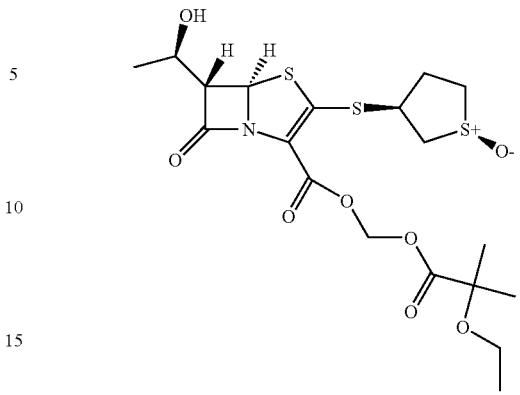

The prodrugs of the present invention may be amorphous or may exist as different crystal forms or polymorphs, including solvates and hydrates. Polymorphs of prodrugs form part of this invention and may be prepared by crystallization of a prodrug of the present invention under various conditions. Polymorphs may also be obtained by heating or melting a prodrug followed by gradual or fast cooling. The presence of polymorphs may be determined by solid probe NMR spectroscopy, IR spectroscopy, differential scanning calorimetry, powder X-ray diffraction or other such techniques. Thus, a recitation of a compound per se is open to its polymorphs, including water or solvent molecules associated therewith.

Preparation

The prodrugs of the present invention can be prepared, e.g., from the free acid of sulopenem according to known methods such as those disclosed herein or in U.S. Pat. No. 3,951,954; U.S. Pat. No. 4,234,579; U.S. Pat. No. 4,287,181; U.S. Pat. No. 4,452,796; U.S. Pat. No. 4,342,693; U.S. Pat. No. 4,348,264; U.S. Pat. No. 4,416,891; U.S. Pat. No. 4,457,924; and U.S. Pat. No. 5,013,729, all of which are incorporated by reference herein in their entireties.

Use

Prodrugs of this invention may be used to treat a variety of hospital and community acquired infections such as respiratory tract, surgical, central nervous system, gastrointestinal, genitourinary, gynecological, skin & soft tissue, and ocular infections and community acquired pneumonia in humans. The antibacterial activity of the prodrugs may be advantageously exploited for preventive use as well. Oral administration is preferred. Biological activity data are given below.

The minimum amount of prodrug administered is a minimum therapeutically effective amount. The maximum amount of prodrug administered is that amount which is toxicologically acceptable. In some embodiments, the amount of sulopenem prodrug administered is that which will maintain the plasma antibiotic concentration of sulopenem above the (90% minimum inhibitory concentration) $MIC_{90}s$ (e.g., about 0.5 μg/mL or about 1 μg/mL) of the infecting pathogens for at least about 30% (e.g., at least about 3.6 hours for BID (2×/day) dosing or 2.4 hours for TID (3×/day)) of the interval between doses. In some embodiments, the blood level is maintained at or above the target level for at least about 40% (e.g., at least about 4.8 hours for BID or 3.2 hours for TID) of the dosing interval.

In general, a daily dose of the sulopenem prodrug for adults may be about 500 mgA (milligrams sulopenem equivalent) to about 6 gA, or about 1 gA to about 5 gA. A regimen of the sulopenem prodrug for adults may be about 500 mgA to about 1500 mgA administered twice a day in about 12 hour intervals. A regimen may be administered over a period of about one week to about two weeks. For certain infections, it may be necessary or desirable to use dosages outside these parameters.

A daily dosage of the prodrug of the present invention can usually be administered from 1 to 4 times daily normally in equal doses. In some embodiments, the prodrug dosage can be about 500 to about 2500 mg BID or TID; about 800 mg to about 1 g BID; or about 2 g BID or TID for more serious infections. In some embodiments, the dosage can be about 7 to about 25 mg/kg BID; about 17 to about 45 mg/kg BID; or about 17 to about 45 mg/kg TID.

In some embodiments, treatment is initiated intravenously with sulopenem itself or other antibiotic and treatment is then continued with an oral prodrug of the present invention.

As discussed further below, the prodrug of Compound 1 was found to provide human blood levels above 0.5 μg/mL for between 3.18 to 4.84 hours upon oral administration of 1000 mg (about 730 mg sulopenem equivalent) of the prodrug. In a different experiment, the prodrug of Compound 1 was found to provide human blood levels above 1 μg/mL for between 4.28 to 5.94 hours upon oral administration of 2000 mg (about 1460 mg sulopenem equivalent) of the prodrug.

Prodrug use can be in conjunction with other active agents. Sulopenem or sulopenem prodrug use can be in conjunction with probenecid or similar acting agent which has an inhibitory effect on renal tubular secretion.

Formulation

The present invention includes pharmaceutical compositions comprising the prodrug compound(s) of the invention formulated for oral administration with or without one or more excipients and/or one or more other active ingredients. The prodrug can be in a solvate or hydrate form.

Oral dosage forms of the present invention can be tablets including chewable tablets, capsules, pills, lozenges, troches, powders, syrups, elixirs, solutions and suspensions, and the like, in accordance with standard pharmaceutical practice. The pharmaceutical composition of the present invention can also be delivered directly to a patient's gastrointestinal tract through a nasogastric tube.

An oral dosage form can in some embodiments contain about 800 to about 2500 mg of the prodrug.

Excipients can be chosen on the basis of the intended dosage form. Nonlimiting examples include polyvinylpyrrolidone, hydroxypropylmethylcellulose, hydroxypropylcellulose, sucrose, gelatin, acacia, gum tragacanth, or corn starch; fillers such as microcrystalline cellulose, lactose, sodium citrate, calcium carbonate, dibasic calcium phosphate, glycine and starch; disintegrants such as corn starch, potato starch, alginic acid, sodium starch glycolate, croscarmellose sodium and certain complex silicates; lubricants such as magnesium stearate, sodium lauryl sulfate and talc; and sweeteners such as sucrose, lactose or saccharin. When a dosage unit form is a capsule, it may contain, in addition to materials of the above type, a liquid carrier such as a fatty oil. Excipients may also include suspending aids such as xantham gum or hydroxypropylmethylcellulose, glidants such as colloidal silica, diluents and bulking agents such as silicon dioxide, flavors, in particular in the case of pediatric oral suspensions and sachets. Stabilizers such as succinic acid can also be employed. Various other materials may be present as coatings or to modify the physical form of the dosage unit. For instance, tablets may be coated with shellac, sugar or both. Modified release dosage forms are also contemplated.

The prodrug(s) will be present in the pharmaceutical composition in an amount sufficient to provide the desired therapeutic dosage amount in the range described herein. The proportional ratio of prodrug to excipients will naturally depend on factors such as the chemical nature, solubility and stability of the active ingredients, as well as the dosage form contemplated. Typically, pharmaceutical compositions of the present invention can contain about 20% to about 95% of prodrug by weight.

Sulopenem Biological Activity

Sulopenem is active against a broad range of pathogens, including hospital pathogens. This includes potent activity against members of the *Enterobacteriaceae* expressing extended-spectrum β-lactamases that confer resistance to cephalosporins (*K. pneumoniae*, ESBL+). In addition, many of these isolates are also resistant to fluoroquinolones. Sulopenem is highly active against many clinically relevant species of anaerobes.

The in vitro activity of sulopenem (the parent acid (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylic acid) was evaluated against pathogens involved in community and hospital infections, as summarized in Table 1.

TABLE 1

| $MIC_{90}$ Values (μg/ml) for Sulopenem | |
|---|---|
| *Staphylococcus aureus* oxacillin-S | 0.125 |
| *Staphylococcus saprophyticus* | 0.5 |
| *Alloiococcus otitidis* | 1 |
| *Streptococcus pyogenes* (Group A) | 0.03 |
| *Streptococcus agalactiae* (Group B) | 0.125 |
| *Streptococcus bovis* (Group D) | 0.06 |
| Viridans *Streptococcus* group | 0.25 |
| *Streptococcus pneumoniae* penicillin-susceptible | 0.03 |
| *Streptococcus pneumoniae* penicillin-intermediate | 0.25 |
| *Streptococcus pneumoniae* penicillin-resistant | 1 |
| *Streptococcus pneumoniae* levofloxacin-resistant | 0.5 |
| *Listeria monocytogenes* | 0.125 |
| *Corynebacterium* spp (not *C. jeikeium*) | 2 |
| *Citrobacter diversus* | 0.06 |
| *Citrobacter freundii* | 0.25 |
| *Enterobacter aerogenes* | 0.5 |
| *Enterobacter cloacae* | 1 |
| *Escherichia coli* | 0.06 |
| *Klebsiella oxytoca* | 0.125 |
| *Klebsiella pneumoniae* | 0.125 |
| *Klebsiella pneumoniae* ESBL+ | 0.25 |
| *Morganella morganii* | 2 |
| *Proteus mirabilis* | 0.5 |
| *Salmonella/Shigella* | 0.125 |
| *Haemophilus influenzae* β-lactamase− | 0.25 |
| *Haemophilus influenzae* β-lactamase+ | 0.5 |
| *Moraxella catarrhalis* β-lactamase− | 0.03 |
| *Moraxella catarrhalis* β-lactamase+ | 0.125 |
| *Legionella pneumophila* | 0.06 |
| *Neisseria meningitides* | 0.06 |
| *Bacteroides fragilis* | 0.5 |
| *Clostridium perfringens* | 0.06 |
| *Prevotella* spp | 0.125 |

Thus, sulopenem is active against a broad range of pathogens, including hospital pathogens that are resistant to cephalosporins and fluoroquinolones. The spectrum supports its broad use in the hospital where the infecting pathogen is identified and the susceptibility to sulopenem is confirmed. This would include a broad list of respiratory indications and surgical indications where mixed flora would likely be involved, particularly as part of a multidrug regimen when mixed infections are suspected.

Prodrug Oral Efficacy

Compounds were profiled for oral efficacy in three different in vivo infection models. The bacterial pathogens used to establish each infection were chosen based on their resistance profiles and abilities to cause infection in models relevant to human disease. The *Klebsiella pneumoniae* isolates 1109 and 6485 are from a collection of recent clinical isolates of extended-spectrum β-lactamase-positive (ESBL$^+$) strains and have elevated MICs to ciprofloxacin and ceftazidime as well as to other β-lactam antibiotics. Both isolates have demonstrated the ability to cause a lethal systemic infection in mice. *Streptococcus pneumoniae* 1095 is a penicillin-tolerant, macrolide-resistant strain that is pathogenic in murine systemic and respiratory tract infection models. The *Haemophilus influenzae* strain Rd/AH5-3 was derived from laboratory strain Rd; a directed point mutation in PBP3 renders this β-lactamase negative strain ampicillin resistant (BLNAR). This strain is capable of causing otitis media in a Mongolian gerbil model of the disease. The results are summarized in Table 2 below.

Murine acute systemic infection model: For this model, CF-1 mice were infected via an intraperitoneal injection of a lethal inoculum of either *K. pneumoniae* 1109, 6485, or *S. pneumoniae* 1095. Four dose groups consisting of eight to ten mice per group were infected and treated, to cover a wide range of dose levels. Mice were administered BID therapy at either 30 minutes/four hours post-infection, or at one/five hours post-infection; the $PD_{50}$ (the dose at which 50% of infected, treated mice survive) was calculated based on the numbers of surviving animals on day four post-infection.

Murine respiratory tract infection model: This model was initiated with an intranasal inoculation of a lethal challenge of *S. pneumoniae* 1095, resulting in pneumonia. Four dose groups consisting of eight to ten mice per group were infected and treated, to cover a wide range of dose levels. BID therapy was initiated eighteen hours post-infection and continued for two days. The number of mice surviving at each dose group on day ten post-infection was used to determine the $PD_{50}$.

Gerbil otitis media model: To establish otitis media, Mongolian gerbils were infected via intrabulla inoculation with a BLNAR strain of *H. influenzae*. Four dose groups consisting of five gerbils per group were infected and treated, to cover a wide range of dose levels. TID therapy was initiated eighteen hours post-infection and continued for two days. On day four post-infection, animals were euthanized, middle ear fluid washes were collected, and bacterial numbers contained therein were determined. $ED_{50}$s were calculated based on bacterial levels; middle ear fluid wash samples with counts lower than 100 colony-forming units/ml were considered cleared.

Data were collected for the compounds of Compounds 1 and 2; for Compound A (drawn below); and for Compound B1, which is the pivaloyloxymethyl ester (POM-ester) of sulopenem ((1R,3S) oxothiolane stereochemistry) drawn below. Compound B2 is the diastereomeric mixture (drawn below).

TABLE 2

In Vivo Efficacy ($PD_{50}$ or $ED_{50}$ in mg/kg)

Compound A:

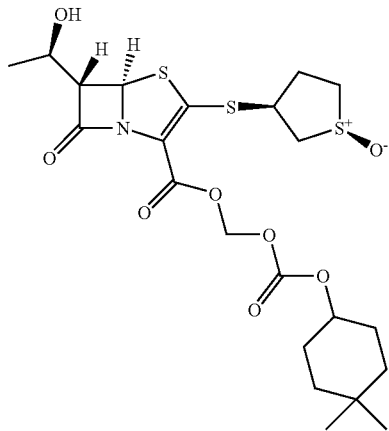

Compound B1:

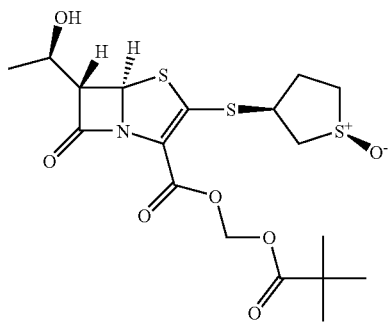

TABLE 2-continued

In Vivo Efficacy ($PD_{50}$ or $ED_{50}$ in mg/kg)

Compound B2:

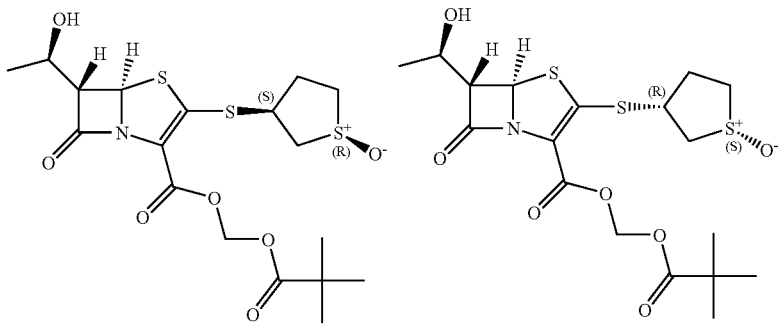

| Model | Cpd. 1 | Cpd. 2 | Cpd. A | Cpd. B1 |
|---|---|---|---|---|
| Murine Acute systemic infection vs. K. pneumoniae 1109 ($PD_{50}$) | 25.1 (13.6-36.6) | 12.5 (12.4-12.6) | 10.1 (3.8-16.4) | 38.2 (27.7-48.7) |
| Murine Acute systemic infection vs. K. pneumoniae 1109 ($PD_{50}$) | 9.0 (8.7-9.3) | 16.2 (15.9-16.6) | 15.3 (9.0-21.6) | 11.4 (11.3-11.5) |
| Murine Acute systemic infection vs. K. pneumoniae 6485 ($PD_{50}$) | 88.6 (87.8-89.4) | 88.3 (68.5-108.2) | 40.7 (29.1-52.3) | >100 |
| Murine Acute systemic infection vs. K. pneumoniae 6485 ($PD_{50}$) | 63.4 (2.1-124.6) | 32.7 (23.7-41.7) | — | >100 |
| Murine Acute systemic infection vs. K. pneumoniae 6485 ($PD_{50}$) | — | 63.4 (58.5-68.3) | — | — |
| Murine Acute systemic infection vs. S. pneumoniae 1095 ($PD_{50}$) | 12.5 (12.4-12.6) | 7.9 (7.3-8.5) | 9.0 (8.7-9.3) | 7.9 (7.3-8.5) |
| Murine Acute systemic infection vs. S. pneumoniae 1095 ($PD_{50}$) | 6.3 (1.5-11.1) | 6.3 (3.4-9.1) | 15.3 (9.0-21.6) | 4.3 (4.2-4.5) |
| Murine Acute systemic infection vs. S. pneumoniae 1095 ($PD_{50}$) | — | 11.0 (8.6-13.5) | — | 9.0 (8.7-9.3) |
| Murine Respiratory tract infection vs. S. pneumoniae 1095 ($PD_{50}$) | 16.4 (9.8-23.0) | 19.7 (18.2-21.2) | 17.8 (0-38.6) | 49.9 (34.7-65.2) |
| Murine Respiratory tract infection vs. S. pneumoniae 1095 ($PD_{50}$) | 12.5 (5.6-19.4) | 38.5 (37.7-39.3) | 20.8 (8.7-50.1) | 18.1 (1.4-34.9) |
| Murine Respiratory tract infection vs. S. pneumoniae 1095 ($PD_{50}$) | 9.5 (4.0-15.0) | — | — | 16.2 (11.5-20.9) |
| Gerbil Otitis media vs. H. influenzae BLNAR ($ED_{50}$) | 8.7 (8.4-9.0) | 5.7 (3.6-7.7) | 6.9 (4.4-9.4) | 12.6 (6.8-18.3) |
| Gerbil Otitis media vs. H. influenzae BLNAR ($ED_{50}$) | 4.5 (4.4-4.6) | 12.6 (6.8-18.3) | 8.7 (8.4-9.0) | 5.7 (5.6-5.7) |

Prodrug Clinical Pharmacokinetics

Clinical pharmacokinetic (PK) data from healthy human volunteers for the sulopenem prodrug compounds of Compound 1, Compound B2 (data from Foulds et al.), and Compound A are summarized in Table 3, below. Compound B2 is a diastereomeric mixture of which the diastereomer configured (1R,3S) at the oxothiolanyl moiety is Compound B1 (see drawings above). Clinical data is not available for prodrug Compound 2.

For Compound 1 and Compound A, six subject received doses in an escalating fashion. Whole blood samples were obtained prior to dosing and at 0.5, 1, 2, 3, 4, 6, 8, and 12 hours post dose and processed for plasma. Serum and plasma samples were then quantified for sulopenem concentrations using validated HPLC methods. Tmax data for Compound A is given as a median and a range.

A total of ten subjects were administered single doses of Compound B2. See Foulds et al., above. Blood samples were obtained prior to dosing and at 0.08, 0.17, 0.33, 0.5, 1, 1.5, 2, 3, 4, 6, and 8 hours and processed for serum following oral administration of Compound B2 at 500 mg equivalent of sulopenem parent compound (five subjects) and 1000 mg equivalent of sulopenem parent compound (five subjects). Foulds et al. also estimates the contributions to the PK from the 1R,3S (Compound B1) and 1S,3R diastereomers present in Compound B2.

increases in systemic exposure. The Compound A data demonstrates at least that increased prodrug lipophilicity does not necessarily translate to improved oral exposure. Lipophilicity (ClogP) was calculated using ACD Labs 9.0 software (LogP/DB; www.acdlabs.com) with the following results: Compound 1: −0.29; Compound A: 0.83; Compound B1: −1.0; Compound B2: −1.0. Further evaluation of Compound A revealed its inherent instability in the gastrointestinal tract. Improved gastrointestinal stability as demonstrated by Compound 1 in vitro using human intestinal juice has correlated to an increase in oral exposure relative to dose.

Prodrug Evaluation and Selection

Prodrugs were evaluated with the ultimate objectives of identifying compounds exhibiting or predicted to exhibit one or more of: favorable PK such as high exposure or bioavailability in humans upon oral administration; a lack of propensity to deplete tissue carnitine; and physicochemical properties favorably suited to practical pharmaceutical formulation and use.

Evaluation of Compound A, among other things, led to a conclusion that prodrug gastrointestinal stability is predicted to play a significant role in oral bioavailability. New prodrug compounds were evaluated and ranked, as detailed below, for stability in the presence of porcine pancrelipase (PPE) and stability in human intestinal juice (HIJ). Efficiency of conversion to sulopenem in human liver homogenate was also con-

TABLE 3

Clinical Pharmacokinetics of Compound 1, Compound B2, and Compound A

| Oral Prodrug | Dose (mg) | Dose Sulo equiv. (mg) | Cmax (ng/mL) | Tmax (hr) | $AUC_{last}$ (hr-ng/mL) | $t_{1/2}$ (hr) |
|---|---|---|---|---|---|---|
| Cpd. 1 | 400 | 292 | 1464 ± 442 | 1.17 ± 0.93 | 3455 ± 670 | 0.85 ± 0.16 |
| " | 600 | 438 | 1508 ± 340 | 1.33 ± 0.82 | 3914 ± 514 | 0.76 ± 0.096 |
| " | 1000 | 730 | 2860 ± 570 | 0.83 ± 0.41 | 6421 ± 1208 | 1.00 ± 0.17 |
| " | 2000 | 1460 | 4667 ± 1181 | 1.33 ± 0.82 | 13131 ± 2101 | 1.10 ± 0.62 |
| Cpd. B2 (Foulds et al.) | 273 | 205 | 1180 ± 280 | NC | 2260 ± 440 | NC |
| Cpd. B2 (Foulds et al.) | 544 | 409 | 1790 ± 490 | NC | 4190 ± 730 | NC |
| Cpd. A | 300 | 196 | 715 ± 303 | 1.0 (0.5-1.5) | 818 ± 480 | NC |
| " | 1000 | 654 | 1380 ± 372 | 0.5 (0.5-1.0) | 2350 ± 642 | 1.11 ± 0.21 |
| " | 1000 fed | 654 fed | 1130 ± 300 | 1.0 (0.5-3.0) | 3900 ± 535 | NC |
| " | 3000 | 1960 | 2260 ± 335 | 1.0 (0.5-1.5) | 5180 ± 1500 | 1.59 ± 0.80 |

The exposure to sulopenem following oral administration of Compound B2 was expressed as fraction absorbed by comparison to intravenous AUCs within the same study (Table 4, Foulds et al.) The fraction absorbed ranged from 38.5 to 33.5% for Compound B2 at sulopenem equivalent doses of 205 to 409 mg. Using the same intravenous data in Table 4 of Foulds et al., a fraction absorbed of 37.1 and 28.0% can be estimated for Compound 1 at sulopenem equivalent doses of 292 and 438 mg, respectively.

Although different dose equivalents were administered, the trend for the prodrugs is of less than dose-proportional sidered a significant parameter pertaining to prodrug oral bioavailability. In vitro endpoints for Liver S9, PPE, and HIJ are summarized in Table 4. Prodrugs were tested according to the following general procedures.

Liver S9 Conversion Efficiency

Prodrugs were evaluated for stability and conversion efficiency in human liver homogenate (S9 fraction). Liver S9 was prepared fresh from liver chunks stored at −70° C. for each analysis completed. Approximately 5 g of frozen liver tissue was homogenized to uniformity in 15 ml of ice cold 100 mM potassium phosphate (pH 7.4) buffer. The homogenate was then centrifuged at 9000 g for 20 minutes at 5° C. to isolate the S9 supernatant fraction. Each incubation was run at a 1:10 dilution of the S9 supernatant in 100 mM potassium phosphate (pH 7.4) buffer. Reactions (1 mL) were initiated by the addition of substrate (50 µM final) at 37° C. Aliquots (75 µL) were obtained at 0, 0.5, 1, 2, 3, 5, 10, and 20 minutes and quenched in 150 µL of 80/20 acetonitrile/100 mM ammonium acetate pH 4.5 containing an internal standard (ampicillin, 5 µg/mL). Samples were centrifuged at 3000 g for 10 minutes and the supernatants transferred to injection vials. First order degradation of the prodrug was monitored by LC/MS/MS as described below. Conversion to sulopenem was expressed as a percentage of the molar equivalent (50 µM) in a fortified sample. Compounds achieving a conversion efficiency of about 75% or greater were generally progressed for further evaluation.

Stability

In these experiments, the contents of one Ku-zyme® HP (USP pancrelipase preparation consisting of: lipase 8000 USP Units, protease 30,000 USP Units, and amylase 30,000 USP Units; Schwarz Pharma Inc., Milwaukee, Wis.) capsule were stirred in 50 mL of 100 mM potassium phosphate pH 7.4 and mixed to uniformity. Each incubation (1 mL) was run at 37° C. and was initiated with the addition of substrate (50 µM final). Aliquots (100 µL) were taken at 0, 0.5, 1, 2, 3, 5, 10, and 20 minutes following substrate addition and quenched with 200 µL of 80/20 acetonitrile/100 mM ammonium acetate pH 4.5 containing an internal standard (ampicillin, 5 µg/mL). Samples were centrifuged at 3000 g for 10 minutes and the supernatants transferred to injection vials. First order degradation of the prodrug was monitored by LC/MS/MS as described below. Compounds achieving a stability half-life of about 10 minutes or greater were progressed for further evaluation.

In Table 4, single values represent an average of two duplicate determinations. Where further determinations were carried out for a given compound, the data are expressed as a mean and standard deviation. All of the compounds were run using a first lot (Lot 1) of ku-zyme.

Compounds 1, A, B1, and B2 were also evaluated using a second lot of ku-zyme (Lot 2), for which data is shown in parentheses.

In the HIJ experiments, HIJ from 4 individual subjects (1 mL each) was pooled with 1 mL of 600 mM potassium phosphate buffer pH 7.4. Aliquots of 300 µL×6 of the buffered human intestinal juice were incubated at 37° C. following fortification of substrate at concentrations of 300, 100, 30, 10, 3, and 1 µM. Two prodrug compounds could be run at the same time. Samples of 35 µL were taken at 0, 0.5, 1, 2, 10, and 20 minutes and quenched with 70 µL of 80/20 acetonitrile/100 mM ammonium acetate pH 4.5 containing an internal standard (ampicillin, 5 µg/mL). Samples were centrifuged at 3000 g for 10 minutes and the supernatants transferred to injection vials. First order degradation of the prodrug was monitored by LC/MS/MS as described below. The percentage of prodrug remaining versus time at each concentration was lifted to a first order decay function to determine the substrate depletion rate constant or $k_{dep}$. A linear-log plot of $k_{dep}$ versus concentration could be lifted with the following equation where:

$$k_{dep} = k_{dep[S]=0} \cdot \left(1 - \frac{[S]}{[S]+K_m}\right)$$

The value of $k_{dep}$ at an infinitesimally low substrate concentration (where $k_{dep} \sim k_{dep[S]=0}$) represents the maximum consumption rate or intrinsic clearance of the system and the $K_m$ is the concentration at which half of the maximal velocity ($V_{max}$) of the system is achieved. In Michaelis-Menton terms, intrinsic clearance $CL_{int}$ represents the ratio of $V_{max}/K_m$ when [S] is well below the $K_m$. Substrate units for these $K_m$ studies are reported in µM and intrinsic clearance ($Cl_{int}$) in mL/min. Generally, compounds with an intrinsic clearance of <0.1 mL/min or a $K_m$ which was three-fold lower than its aqueous solubility (in order to saturate enzymatic action) were progressed for further evaluation.

Solubility

Equilibrium solubility was determined in 25 mM phosphate buffer (pH 5) at ambient temperature. Vials containing excess prodrug in phosphate buffer were rotated for up to 48 hours. After the equilibrium period, samples were pulled, filtered through 0.45 µm Gelman Acrodisc Nylon syringe filter and analyzed for drug concentration using HPLC. The HPLC conditions were: Column: C18, SymmetryShield RP, Waters, 4.6×150 mm, 3.5 micron; Mobile phase A: Acetonitrile; Mobile phase B: 0.1% TFA in water; Flow rate: 1 mL/min; Run Time: 30 min; Inj. vol: 20 µL; Detection: 210 nm; Dissolving solvent: Acetonitrile/water (50:50 v:v). Results are shown in Table 4.

| Gradient used: | | |
| --- | --- | --- |
| Time | % A | % B |
| 0 min | 5 | 95 |
| 25 min | 95 | 5 |
| 27 min | 5 | 95 |
| 30 min | 5 | 95 |

Melting Point

Melting points were determined on a MEL-TEMP 3.0 capillary melting point apparatus and are uncorrected.

Quantitation of Prodrug

Quenched samples from these in vitro experiments were quantified using LC/MS/MS. Separation was achieved on a Phenomonex Primesphere C18-HC column (5 µm, 30×2.0 mm) using a binary gradient made up of Solvent A (95% water/5% acetonitrile/0.1% acetic acid) and Solvent B (5% water/95% acetonitrile/0.1% acetic acid). The injection volume was 20 µL. The column was equilibrated and the gradient initiated with 100% A at a flow rate of 1000 µL/min. The gradient was ramped to 100% B within 0.4 min., and then back to 100% A by 0.9 min. Ampicillin was used as an internal standard (5 µg/mL). The effluent was analyzed by a mass spectrometer detector (Sciex API 3000) fitted with a turbo ion spray interface and operated in positive ion mode with a declustering potential of 10V, temperature of 400° C. and collision energy of 25V. All prodrugs, sulopenem, and ampicillin, were monitored by MRM transitions of the protonated parent mass to a major fragment ion in the collision induced dissociation spectra. The typical dynamic range of the assay ranged from 10.0 to 10,000 ng/mL.

TABLE 4
| Cpd. | Structure | S9 % Conv. (avg) | PPE Half Life (min) | HIJ Km (μM) (avg) | HIJ Clint (mL/min) (avg) | solubility (μg/mL) |
|---|---|---|---|---|---|---|
| 1 | 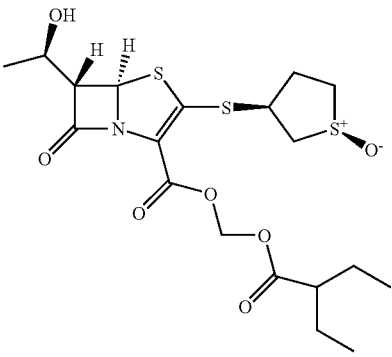 | 100 | 11.7 ± 3.8 (17.9 lot 2) | 91 | 0.07 | 1209 |
| 2 | 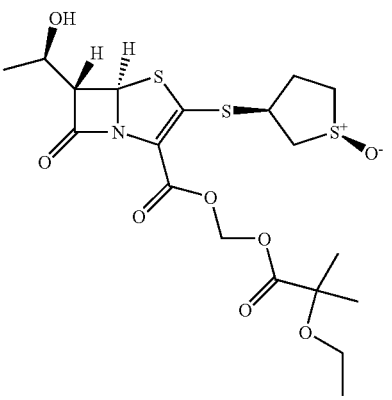 | 76 | 19.1 | 105 | 0.13 | 2900 |
| A | 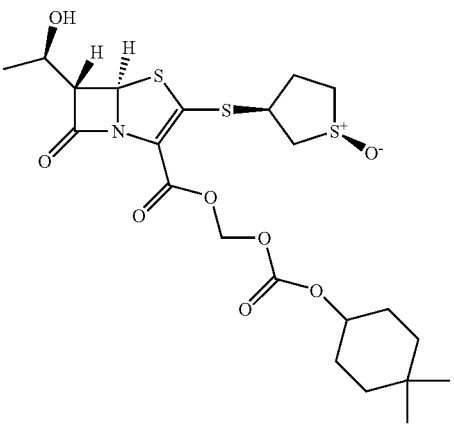 | 100 | 3.9 ± 1.1 (6.3 lot 2) | 300 | 0.38 | 136 |
| B1 | 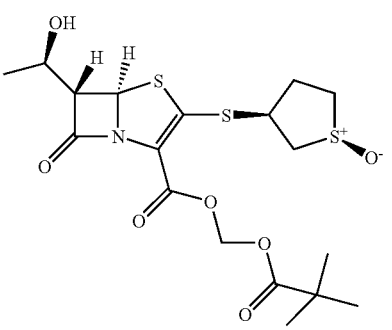 | 100 | (22.5 ± 0.6 lot 2) | 29 | 0.11 | 389 |

TABLE 4-continued
| Cpd. | Structure | S9 % Conv. (avg) | PPE Half Life (min) | HIJ Km (μM) (avg) | HIJ Clint (mL/min) (avg) | solubility (μg/mL) |
|---|---|---|---|---|---|---|
| B2 | 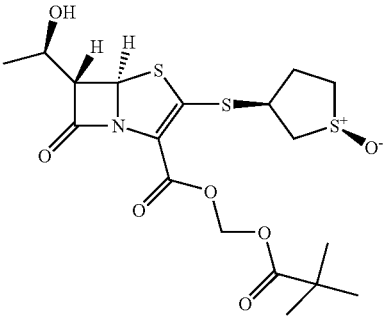 | 94 | 11.6 (19.6 lot 2) | 40 | 0.09 | — |
|  | 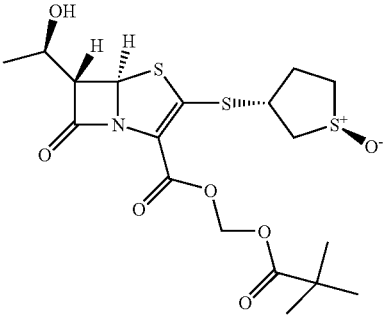 |  |  |  |  |  |
| C | 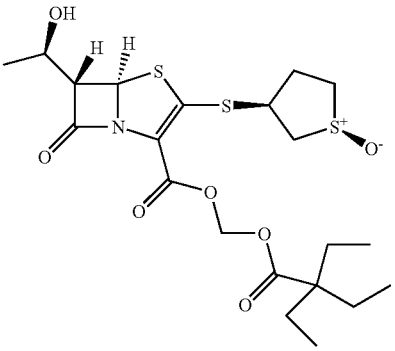 | 2.4 | 21.1 | — | — | — |
| D | 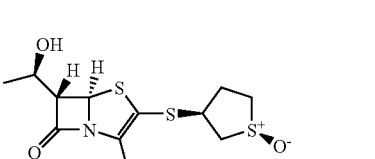 | — | — | — | — | — |

TABLE 4-continued

| Cpd. | Structure | S9 % Conv. (avg) | PPE Half Life (min) | HIJ Km (μM) (avg) | HIJ Clint (mL/min) (avg) | solubility (μg/mL) |
|---|---|---|---|---|---|---|
| E | 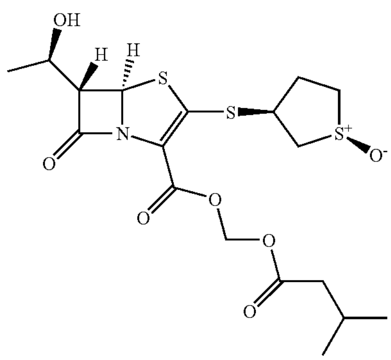 | — | 6.4 | — | — | — |
| F | 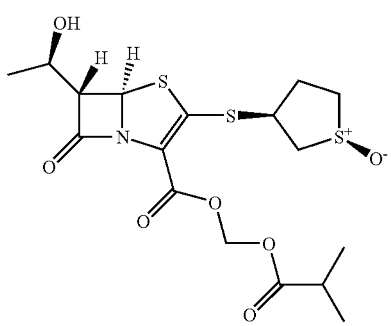 | — | 4.7 | — | — | — |
| G | 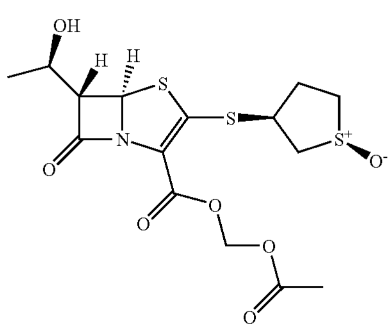 | 100 | 21.2 | 390 | 0.18 | — |
| H | 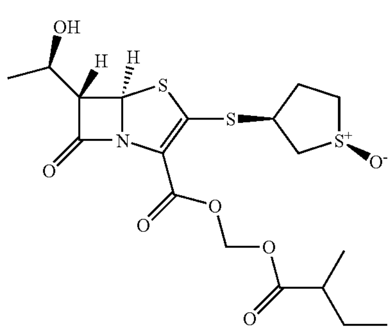 | — | 6.8 | — | — | — |

TABLE 4-continued

| Cpd. | Structure | S9 % Conv. (avg) | PPE Half Life (min) | HIJ Km (μM) (avg) | HIJ Clint (mL/min) (avg) | solubility (μg/mL) |
|---|---|---|---|---|---|---|
| I | 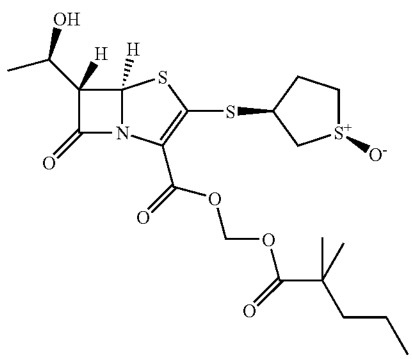 | 95 | 14.4 | — | — | — |
| J | 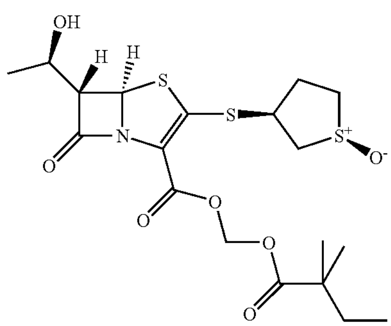 | 86.8 | 11 | — | — | — |
| K | 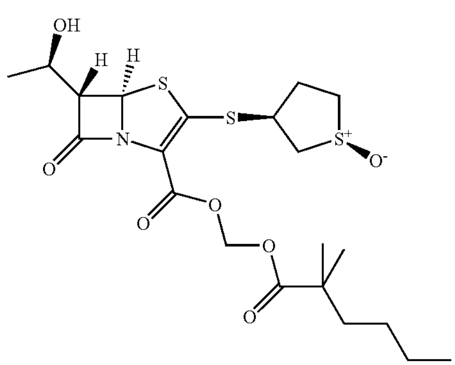 | 47.2 | 14.5 | — | — | — |
| L | 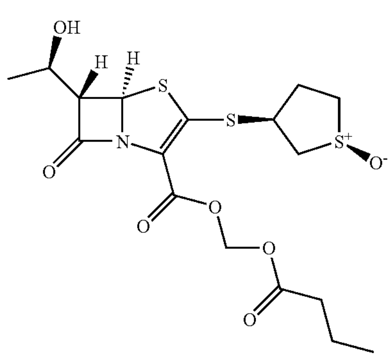 | — | — | — | — | — |

TABLE 4-continued

| Cpd. | Structure | S9 % Conv. (avg) | PPE Half Life (min) | HIJ Km (µM) (avg) | HIJ Clint (mL/min) (avg) | solubility (µg/mL) |
|---|---|---|---|---|---|---|
| M | 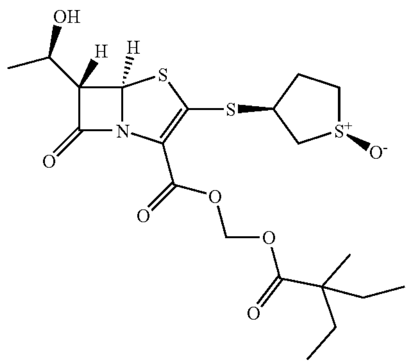 | 20.4 | 39.4 | — | — | — |
| N | 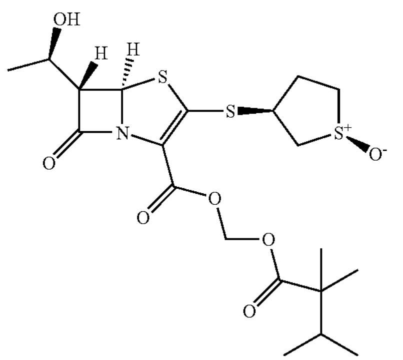 | 14.1 | 11.1 | — | — | — |
| O | 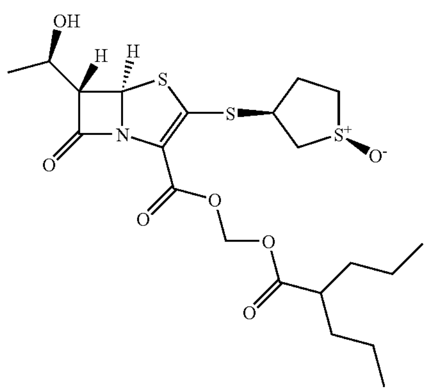 | — | 8.3 | — | — | — |
| P | 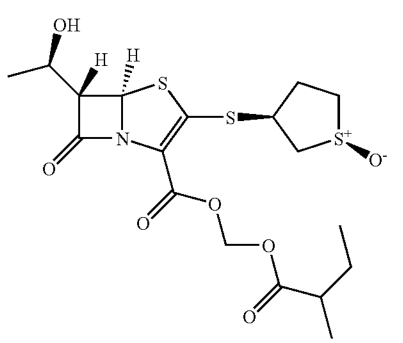 | — | 4.2 | — | — | — |

TABLE 4-continued

| Cpd. | Structure | S9 % Conv. (avg) | PPE Half Life (min) | HIJ Km (μM) (avg) | HIJ Clint (mL/min) (avg) | solubility (μg/mL) |
|---|---|---|---|---|---|---|
| Q | 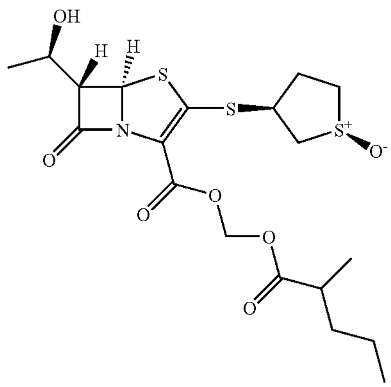 | — | 4.8 | — | — | — |
| R | 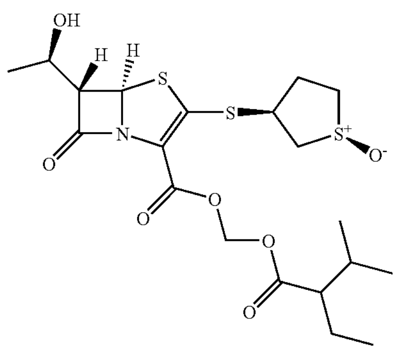 | 0 | 5.3 | — | — | — |
| S | 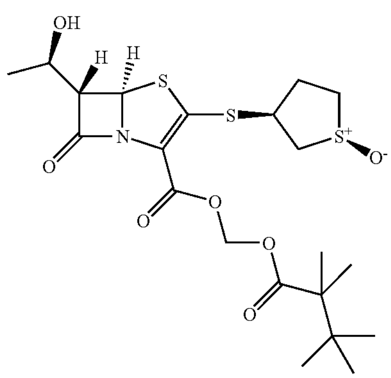 | — | 6.3 | — | — | — |
| T | 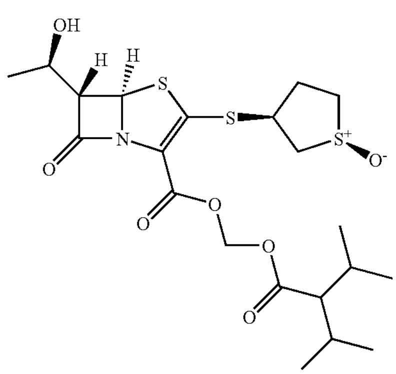 | — | 7.7 | — | — | — |

TABLE 4-continued

| Cpd. | Structure | S9 % Conv. (avg) | PPE Half Life (min) | HIJ Km (μM) (avg) | HIJ Clint (mL/min) (avg) | solubility (μg/mL) |
|---|---|---|---|---|---|---|
| U | 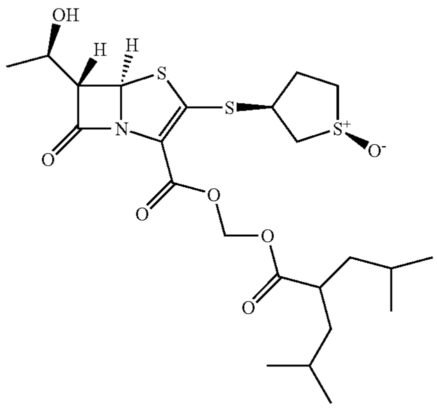 | — | 6.4 | — | — | — |
| V | 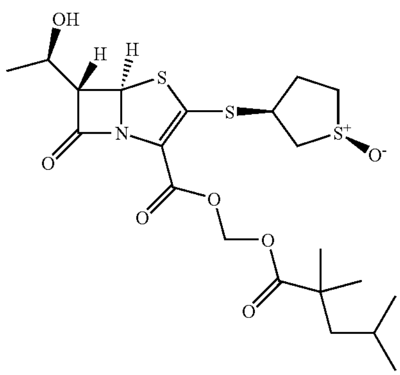 | — | 10.5 | — | — | — |
| W | 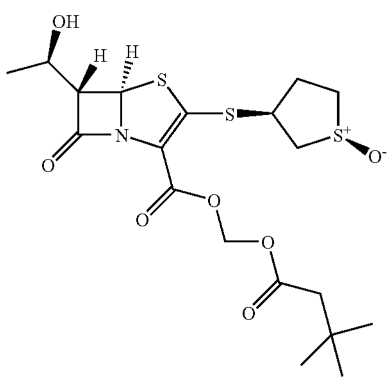 | — | 7.6 | — | — | — |
| X | 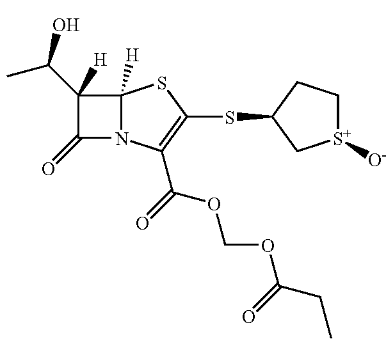 | — | 4.7 | — | — | — |

TABLE 4-continued

| Cpd. | Structure | S9 % Conv. (avg) | PPE Half Life (min) | HIJ Km (μM) (avg) | HIJ Clint (mL/min) (avg) | solubility (μg/mL) |
|---|---|---|---|---|---|---|
| Y | 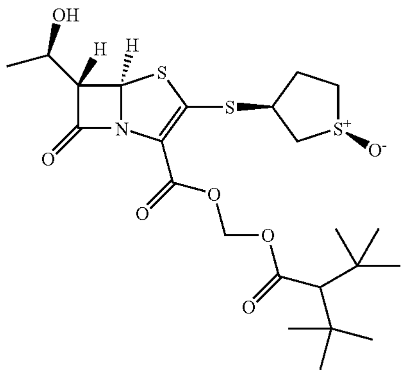 | — | 8 | — | — | — |
| Z | 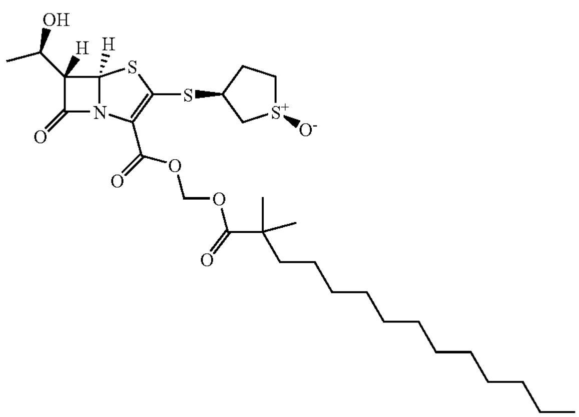 | — | — | — | — | — |
| AA | 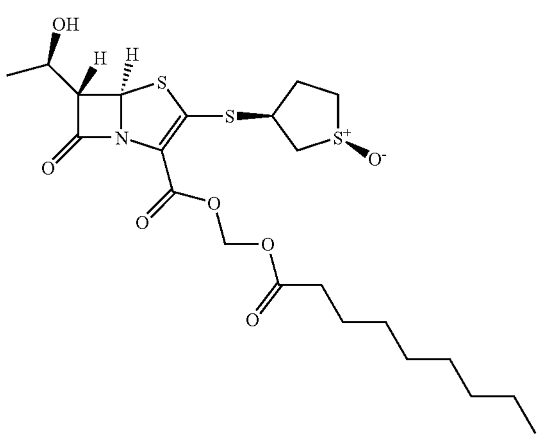 | — | — | — | — | — |

Carnitine Depletion

Small alkyl acids like pivalic acid which are fully substituted at the carbon alpha to the carboxylate are not sufficiently catabolized through β-oxidation. As a result, carnitine is acylated and acyl carnitine accumulates in the tissue and bloodstream, depleting free concentrations of carnitine. As such, acids that are fully substituted at the alpha carbon provide the potential to decrease carnitine stores in the body. See Brass, above. This has been shown in short course therapies with pivalic acid-containing prodrugs wherein carnitine depletion resulted in impaired fatty acid oxidation and impaired ketogenesis. See Abrahamsson et al. *Biochem. Med. Metab. Biol.,* 52, 18-21 (1994). A prodrug sidechain that is eliminated rapidly and safely and which does not deplete carnitine stores in the body would be desirable. The metabolic conversion of certain small alkyl acids to their glucuronide conjugates provides an efficient pathway of elimination from the body. Valproic acid, for instance, has been shown to be eliminated extensively via glucuronidation (See Zaccara et al. *Clin. Pharmacol.,* 15, 367-389 (1988)), while pivalic acid is excreted almost entirely as its acylcarnitine conjugate in humans. See Totsuka et al. *Antimicrob. Agents and Chemother.,* 36, 757-761 (1992). It can be appreciated that subtle changes in structure can translate to substantial differences in metabolic disposition of these alkyl acids.

The metabolic conversion of certain small alkyl acids to their glucuronide conjugates provides an efficient pathway of elimination from the body. Valproic acid, for instance, has been shown to be eliminated extensively via glucuronidation (See Zaccara et al. *Clin. Pharmacol.,* 15, 367-389 (1988)), while pivalic acid is excreted almost entirely as its acylcarnitine conjugate in humans.

Of interest was a comparison between Compound 1 and Compound B1 in terms of the prodrug side chains' tendency or lack thereof to deplete plasma carnitine following metabolism of the intact prodrug. This was evaluated in vivo using an acute model of carnitine depletion in Sprague-Dawley rats. To understand the potential impact in vivo, radiolabeled pivalic acid (Compound B1 side chain) and 2-ethylbutyric acid (Compound 1 side chain) were administered orally at a dose of 200 mg/kg BID for 4 days to two separate groups of animals. The pivalic acid was labeled with $^{14}C$ at the carbonyl carbon (1-position) and had a specific activity of 0.482 µCi/mg. The 2-ethylbutyric acid was labeled with $^{14}C$ at the carbon adjacent to the carbonyl carbon (2-position) and had a specific activity of 0.503 µCi/mg. Doses were administered in 100 mM sodium phosphate pH 6.6 at a dose volume of 10 mL/kg. Blood samples were obtained at 24 hour intervals following initiation of the study, processed for plasma and assayed for carnitine levels by LC/MS/MS. A vehicle control consisting of oral administration of an equal volume of buffer without compound was completed as a baseline comparison. As shown in FIG. 1, animals receiving 200 mg/kg BID of pivalic acid showed decreased levels of plasma carnitine relative to vehicle control. By contrast, animals receiving the same dose of 2-ethylbutyric acid over the course of 4 days demonstrated statistically insignificant changes in plasma carnitine, suggesting this compound does not cause carnitine depletion.

Figure 2:
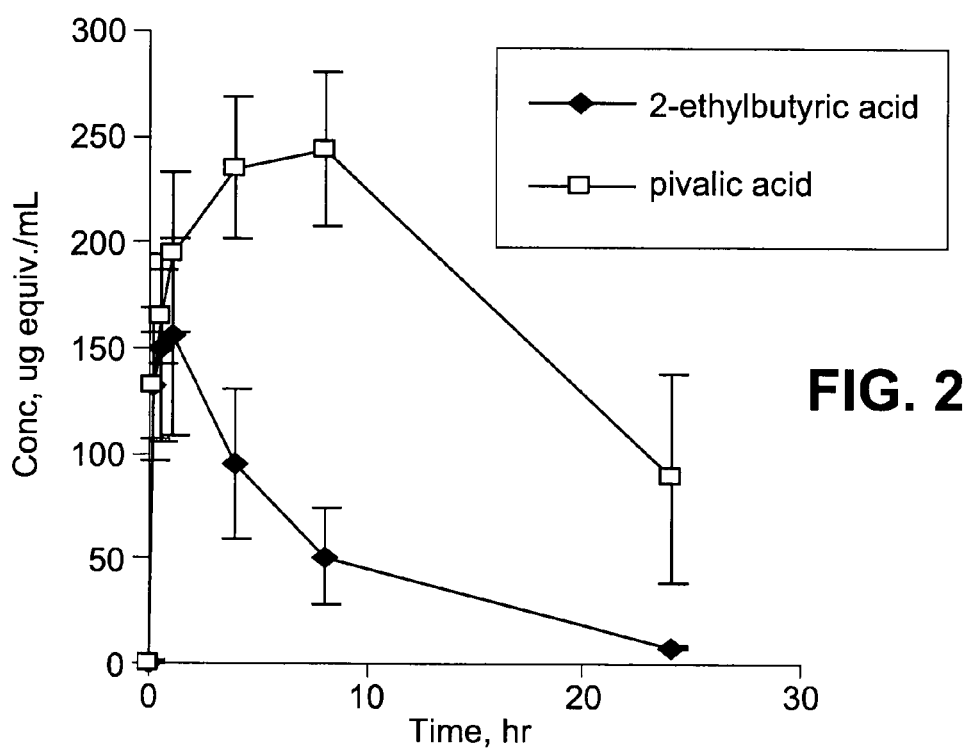
FIG. 2 shows the results of a clearance study where rats were orally administered a single 200 mg/kg dose of radiolabeled pivalic acid and 2-ethylbutyric acid.

A separate study using a single 200 mg/kg dose of each radiolabeled compound (pivalic acid and 2-ethylbutyric acid) was completed in rats to determine systemic exposure of dose following oral administration. The oral administration route was chosen because it is expected that the majority of hydrolysis of the prodrugs will occur within the intestine prior to entering systemic circulation. Plasma samples were obtained prior to dosing and at 0.25, 0.5, 1, 4, 8, and 24 hr post-dose. Samples were quantified for radioactivity by liquid scintillation counting and the counts were converted to µg equivalents/mL. As shown in Table 5 and FIG. 2, once absorbed, radioactivity associated with 2-ethylbutyric acid is cleared 4.5 fold faster than pivalic acid, reflecting efficient metabolic processing and excretion of the compound.

Accordingly, oral administration of prodrug Compound 1 is not expected to result in carnitine depletion, whereas administration of Compound B1 is.

TABLE 5

Pharmacokinetics of Total Radioactivity in Sprague-Dawley Rats Following Oral Administration of $^{14}C$-pivalic acid or $^{14}C$-2-ethylbutyric acid at a dose of 200 mg/kg (100 µCi/kg)

| Administered Compound | Cmax (µg eq./mL) | Half-life (hr) | AUC (hr * µg eq./mL) | CL/F (mL/hr/kg) |
|---|---|---|---|---|
| pivalic acid | 247 ± 36 | 13.8 ± 6.7 | 6624 ± 2948 | 35.6 ± 14.3 |
| 2-ethylbutyric acid | 158 ± 47 | 5.7 ± 0.8 | 1332 ± 402 | 163.3 ± 53.5 |

Other Properties

For purposes of convenient formulation and suitability as a pharmaceutical product, in some embodiments, the compound is preferably solid at room temperature, preferably readily forms a crystalline solid, and is reasonably stable to degradation.

Discussion

Compound 1 was determined to exhibit a favorable combination of properties. In addition to being crystalline and adequately soluble in water, Compound 1 was fully converted to sulopenem in the liver S9 experiments, exhibited a relatively long PPE half-life, and a relatively low intrinsic clearance and saturation of intestinal enzymes in human intestinal juice. Based on this data, Compound 1 was predicted to exhibit favorable clinical PK, which was confirmed by the clinical data described above. Moreover, as evidenced by its structure and the carnitine work described herein, Compound 1 does not carry a carnitine liability. Thus, Compound 1 combines at least all of: good oral bioavailability, lack of carnitine liability, and favorable physical properties. In contrast, other prodrugs, in particular others bearing alkyl side chains, were not predicted to match these attributes. For instance, several of Compounds C to AA have a tertiary carbon alpha to the ester carbonyl group of the promoiety (e.g., Compound C). These are predicted to have a potential carnitine liability. Other of the test compounds had relatively low PPE stability and/or S9 conversion, predictive of lower GI stability and oral bioavailability. Still others were not tested due to difficulties in obtaining readily testable samples. See Table 4.

Prodrug Compound 2 also was shown to have favorable attributes, which include its predicted GI stability and bioavailability, and physical properties. See Table 4.

COMPOUND EXAMPLES

The present invention will be further illustrated by means of the following nonlimiting examples. Crystalline sulopenem, which was used in the present exemplification, was prepared according to Example 11 of U.S. Pat. No. 5,013,729.

Example 1

(2-Ethyl-1-oxobutoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate (Compound 1).

The title compound was prepared according to the following scheme and description.

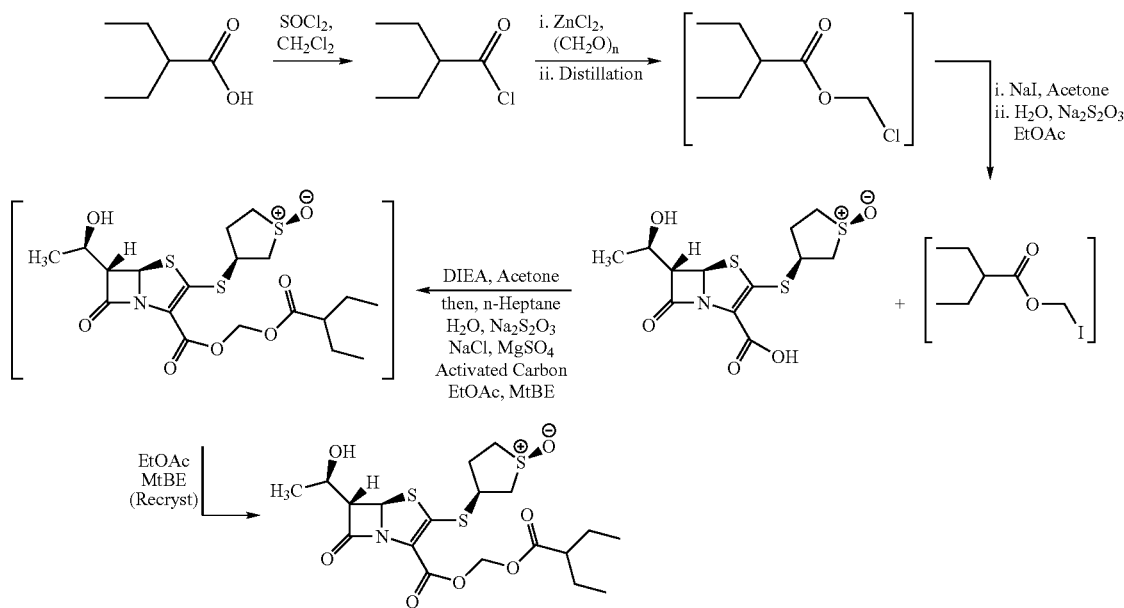

Step 1: 2-Ethyl butyric acid (1500 g) was added to a solution of thionyl chloride (1800 g) in dichloromethane (0.75 L) over 1 hour. The mixture was heated to reflux and was monitored by GC (gas chromatography). After approximately 2 hours, the reaction mixture was concentrated via distillation at atmospheric pressure. It was then cooled to 22° C., dichloromethane (0.75 L) was added, and the mixture was concentrated once again at atmospheric pressure. Due to the extreme corrosiveness of the reagents used, all exhaust gases were passed through a wet caustic scrubber.

Step 2: Meanwhile, a mixture of zinc chloride (18 g) and paraformaldehyde (480 g) was prepared. The semi-crude, neat acid chloride was added to this mixture over 1 hour at ambient temperature with mechanical stirring. After a small induction period, a significant exotherm was observed. The temperature of the reaction mixture increased from ambient (25° C.) to 50° C. over 5 minutes. The rate of addition was slowed to control the exotherm, and maintain the reaction at 50° C. After complete addition, the reaction mixture was allowed to cool and was stirred at ambient temperature for an additional 18 hours.

n-Heptane (4 L) and 10% aqueous sodium bicarbonate solution (9 L) were then charged and the phases were separated. The aqueous phase was extracted with n-heptane (3.4 L). The combined organic phases were filtered and distilled under vacuum to afford the crude product. The product was purified by vacuum distillation (10-20 mmHg) to give 587 g of 2-ethylbutyric acid chloromethyl ester.

Step 3: 2-Ethyl butyric acid chloromethyl ester (700 g) was dissolved in acetone (3 L). To this solution was added sodium iodide (1.0 kg). The resulting reaction mixture was heated at reflux until reaction completion (2 h (hours), monitored by GC). The solution was then cooled to ambient temperature where tert-butyl methyl ether (7 L) and 5% aqueous sodium thiosulfate (4 L) were added. The phases were separated and the organic phase was washed with aqueous sodium thiosulfate (4 L), low pyrogen water (4 L) and 10% sodium chloride solution (4 L). The organic layer was dried over magnesium sulfate (350 g), filtered, and the filter cake was washed with tert-butyl methyl ether (2×0.7 L). The filtrate was evaporated to a small volume (ca. 2 L) to give 2-ethyl butyric acid iodomethyl ester, as a solution in tert-butyl methyl ether.

Step 4: The semi-crude tert-butyl methyl ether solution of 2-ethyl butyric acid iodomethyl ester from Step 3 was added to a slurry of sulopenem (750 g) in acetone (5.9 L). N,N-Diisopropylethylamine (DIEA) (319 g) in acetone (0.5 L) was added and the mixture was stirred at ambient temperature until reaction completion. Low pyrogen water (6.5 L) and heptane (3.75 L) were added and the phases were separated. The aqueous layer was extracted first with heptane (5 L) and then with ethyl acetate (2×6 L). The ethyl acetate extracts were combined and washed with 5% aqueous sodium thiosulfate (6 L), low pyrogen water (6 L) and 10% aqueous sodium chloride (6 L). The organic extract was treated with activated carbon (75 g) and magnesium sulfate (150 g), then was filtered. The filter cake was washed with ethyl acetate (2×1 L) and the filtrate was evaporated to dryness to provide the crude product (0.8 kg). Ethyl acetate (2.4 L) was added and the solution was heated (45° C.) to achieve dissolution. This solution was then hot-filtered and tert-butyl methyl ether (4.7 L) was added. The resulting slurry was granulated for 10 minutes at 40° C. to 50° C. and was then cooled slowly to less than 10° C. The resulting solid was collected, washed with a 1:2 mixture of ethyl acetate and tert-butyl methyl ether (4×0.5 L) and dried to constant weight under vacuum at up to 50° C. to give 0.57 kg of the desired product (60% yield).

Step 5: The semi-crude product (0.55 kg) was slurried in ethyl acetate (1.65 L) at ambient temperature. The temperature was then adjusted to ca. 50° C. to achieve dissolution. This solution was hot-filtered to remove insoluble impurities then tert-butyl methyl ether (3.6 L) was added. The resulting solution was slowly cooled to less than 5° C. to initiate crystallization. The solid product was collected, washed with a 1:2 mixture of ethyl acetate and tert-butyl methyl ether (4×150 mL) and dried to constant weight under vacuum at up to 50° C. to give 0.48 kg of the desired product (86% yield). The crystalline material was determined to be non-solvated.

$^1$H NMR (DMSO-d$_6$, 400 MHz): 5.71 (m, 3H), 5.19 (d, 1H, J=4.56 Hz), 3.92 (m, 2H), 3.81 (m, 1H), 3.70 (m, 1H), 2.96 (m, 1H), 2.80 (m, 1H), 2.65 (m, 2H), 2.36 (m, 1H), 2.19 (m, 1H), 1.45 (m, 4H), 1.10 (d, 3H, J=6.22 Hz), 0.78 (t, 6H).

MP: 105° C.; Mass. Spec.: (M+H)$^+$ 478.

MW: 477.92 g/mol; Molec. Form.: C$_{19}$ H$_{27}$ N O$_7$ S$_3$.

Aqueous solubility (pH 5 phosphate buffer, 25° C.): 1209 µg/mL.

Figure 3:
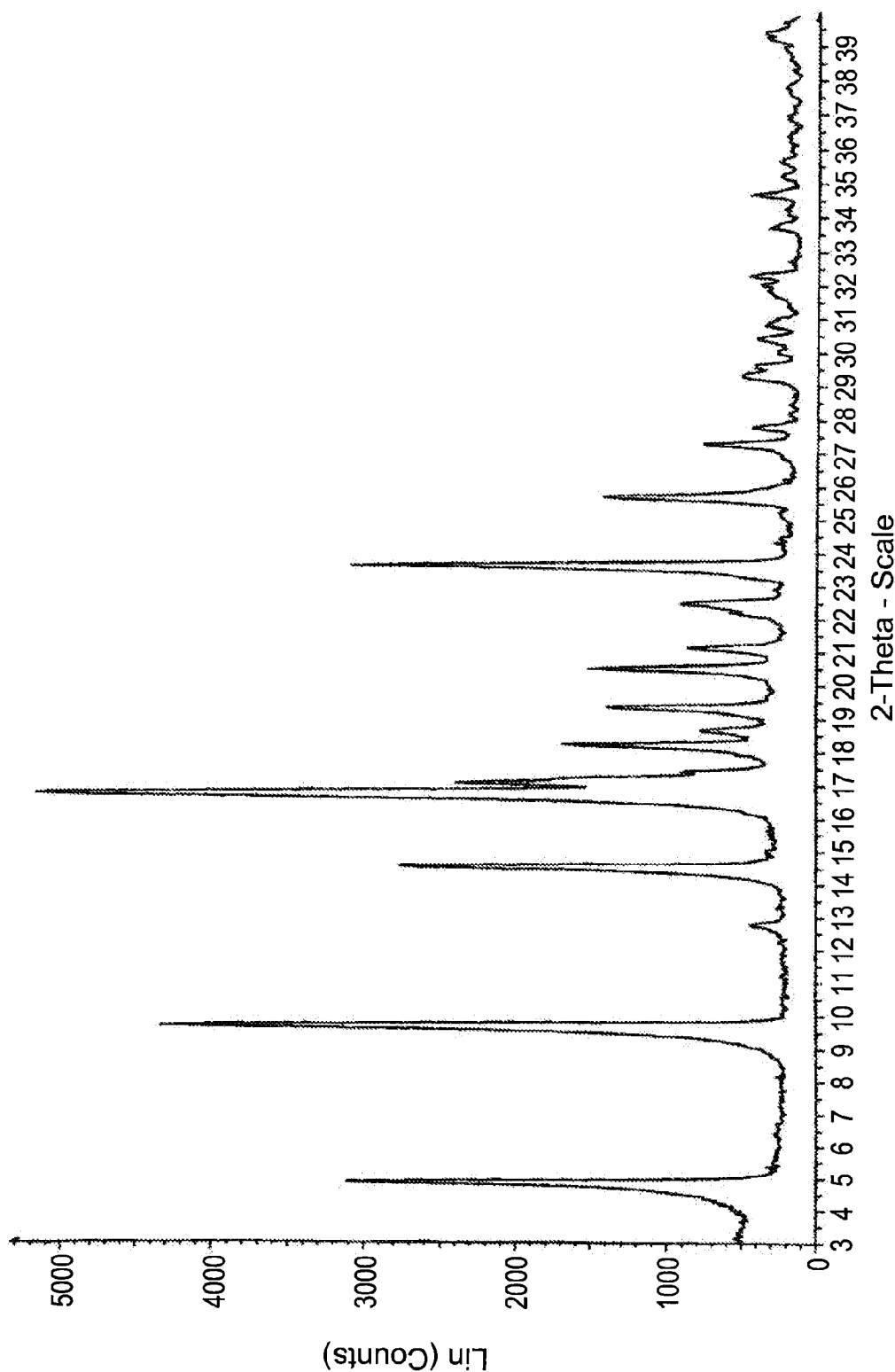
FIG. 3 shows the x-ray diffraction pattern for (2-ethyl-1-oxobutoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate (Compound 1).

Crystals of Compound 1 prepared in the manner of Step 5 above were submitted for X-ray powder diffraction. Samples were analyzed on a Siemens D500 Automated Powder Diffractometer equipped with a graphite monochromator and a Cu (λ=1.54 Å) X-ray source operated at 50 kV, 40 mA. Two-theta calibration was performed using an NBS mica standard. Sample preparation was performed using a zero background sample plate. The diffraction pattern of these crystals of Compound 1 is shown in FIG. 3 and tabulated in FIG. 5.

Example 2

(2-Ethoxy-2-methyl-1-oxopropoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate (Compound 2)

The title compound was prepared according to the following scheme and description.

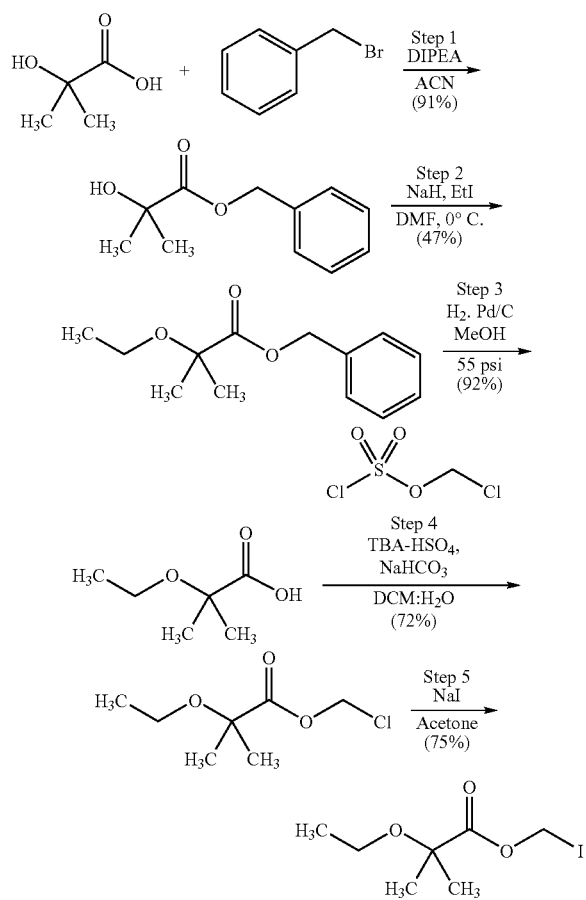

-continued

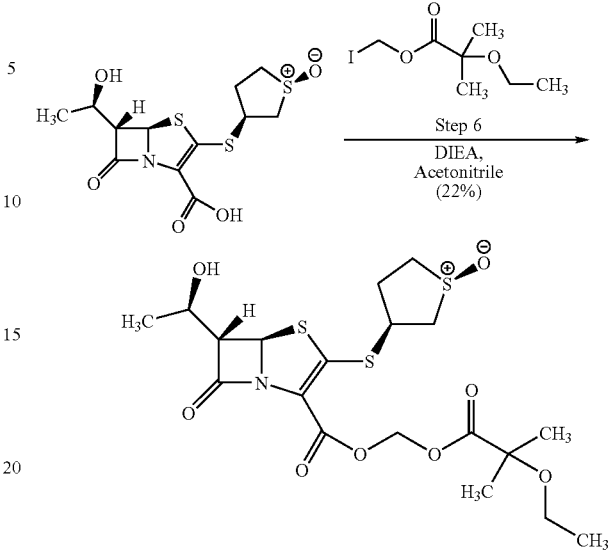

In steps 1-4, 2-hydroxy-isobutyric acid was protected with benzyl bromide, alkylated with ethyl iodide, deprotected, and esterified to afford 2-ethoxy-isobutyric acid chloromethyl ester.

In step 5, in a suitable reaction flask, sodium iodide (23.9 g, 159.45 mmol, 1.6 eq.) was dissolved in acetone (96 mL). 2-Ethoxy-isobutyric acid chloromethyl ester (18 g, 99.65 mmol, 1 eq.) was then added as a solution in additional acetone (18 mL), and the resulting reaction mixture was heated at reflux under a nitrogen atmosphere for approximately 2 h. The reaction was monitored by GC. Upon complete conversion, the reaction was allowed to cool to room temperature with stirring. The reaction was then partitioned between heptanes (120 mL) and 10% aqueous sodium thiosulfate solution (105 mL). The contents of the reaction vessel were stirred for at least 5 minutes, and then the phases were allowed to separate. The light organic phase was set aside, and the heavy aqueous phase was discarded. Organics were then washed with a second portion of 10% aqueous sodium thiosulfate solution (105 mL), and the heavy phase was once again discarded after separation. The organic layer was then washed with 10% aqueous sodium chloride (105 mL). The heavy aqueous phase was discarded, and the organics were concentrated under reduced pressure (<35° C.). This provided 16.26 g of 2-ethoxy-isobutyric acid iodomethyl ester that was used in subsequent chemistry without additional purification (assay: ~60%).

In Step 6, to a suitable reaction vessel under a nitrogen atmosphere was added sulopenem (13.92 g, 39.83 mmol, 1 eq.) and acetone (110 mL). 2-Ethoxy-isobutyric acid iodomethyl ester (16.26 g, 59.9 mmol, 1.5 eq. at 100% potency) in acetone (14 mL) was then added, and the suspension was stirred for a minimum of 10 min. N,N-Diisopropylethylamine (5.11 g, 39.54 mmol, 1 eq.) in acetone (14 mL) was then added, maintaining an internal temp of <35° C. (exothermic). The reaction mixture was stirred at ambient temperature overnight (after ca. 2 h. the sulopenem had dissolved). The reaction mixture was then partitioned between heptanes (80 mL) and water (129 mL), and the contents of the reaction vessel were stirred for at least 5 minutes. The phases were separated, and the light organic phase was discarded. The heavy phase was washed with additional heptanes (80 mL). Once again, the phases were separated, and the light organic phase was discarded. The contents of the reaction vessel were then concentrated by approximately 50% under reduced pressure, while maintaining an internal temperature of less than 35° C. Ethyl acetate (120 mL) was added, and the contents of the reaction vessel were stirred for at least 5 minutes. The phases were allowed to separate, and the light organic phase was set aside. The heavy aqueous phase was back-extracted with additional ethyl acetate (2×120 mL). Combined organics were washed with 10% aqueous sodium thiosulfate (120 mL), water (120 mL) and 10% aqueous sodium chloride (120 mL). The organics were then treated with activated carbon (2.9 g), celite (2.9 g) and magnesium sulfate (MgSO$_4$) (8.2 g) at ambient temperature and stirred for at least 1 h. After removal of these solids by filtration, the solution was concentrated under reduced pressure, while maintaining an internal temperature of less than 45° C. (ethyl acetate bp 76.5-77.5° C.).

Step 7: The resulting crude Compound 2 (23 g) in ethyl acetate (100 mL) was warmed nearly to reflux to fully dissolve the solids, and then tert-butyl methyl ether (100 mL) was added gradually, maintaining an internal temperature of 60° C. to reflux. The resultant mixture was stirred slowly at 60° C. to reflux for 5 minutes, and then was granulated for a minimum of 1 h at 5-15° C. The white to off-white product was filtered, washed with methyl t-butyl ether (MTBE) (28 mL) and dried under vacuum at ambient temperature for at least 16 h. This gave the product (Compound 2) as a white solid, (12.57 g, 63.9% yield).

Figure 4:
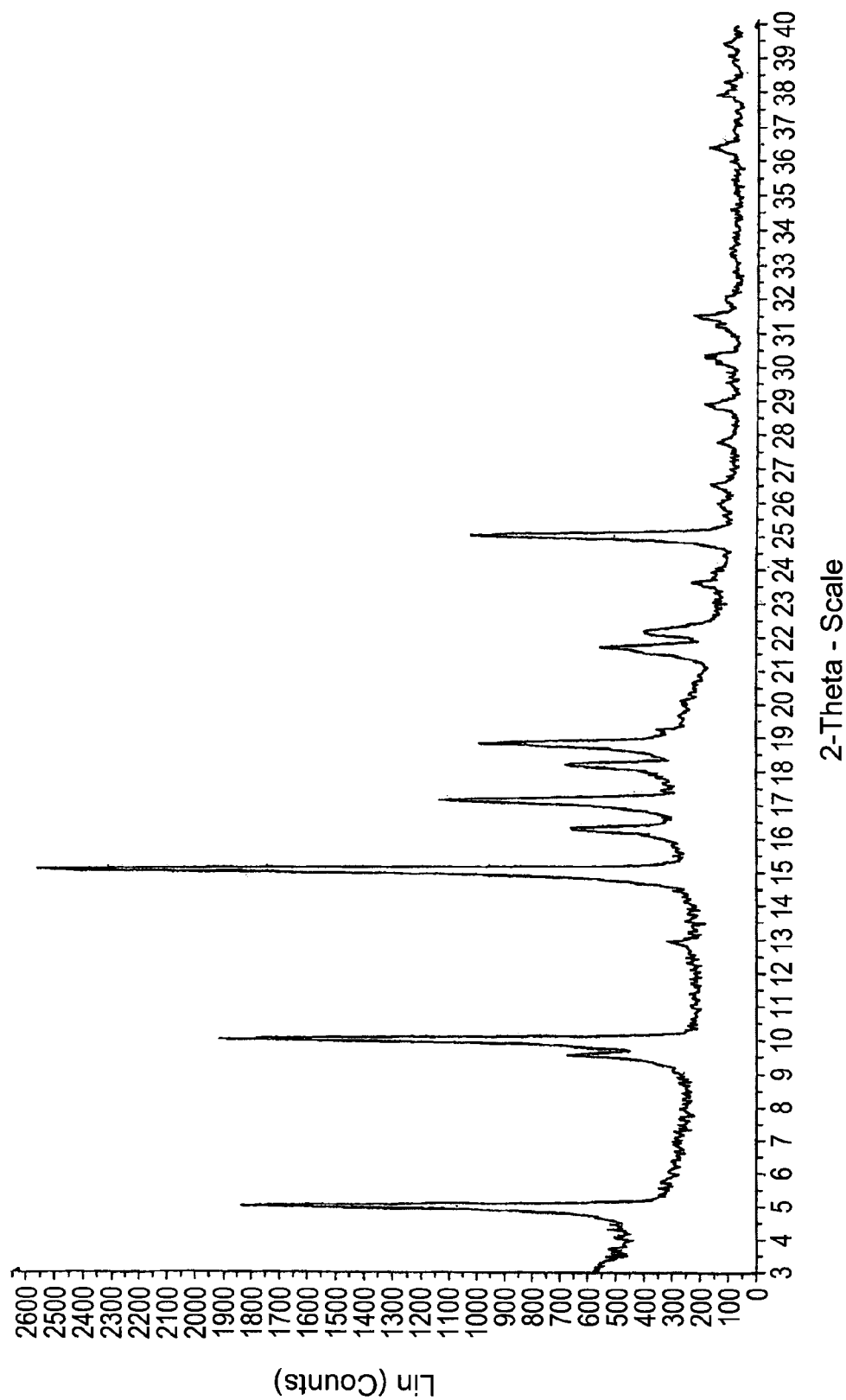
FIG. 4 shows the x-ray diffraction pattern for (2-ethoxy-2-methyl-1-oxopropoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate (Compound 2).

Crystals from this product were submitted for X-ray powder diffraction. Samples were analyzed on a Siemens D500 Automated Powder Diffractometer equipped with a graphite monochromator and a Cu (λ=1.54 Å) X-ray source operated at 50 kV, 40 mA. Two-theta calibration was performed using an NBS mica standard. Sample preparation was performed using a zero background sample plate. The diffraction pattern is shown in FIG. 4 and tabulated in FIG. 6.

$^1$H NMR: (d$_6$-DMSO, 400 MHz): 5.83 (d, 1H, J=5.81 Hz) 5.73 (m, 2H), 5.20 (m, 1H), 3.92 (m, 2H), 3.81 (m, 1H), 3.70 (m, 1H), 3.28 (q, 2H, J=7.05 Hz), 2.96 (m, 1H), 2.80 (m, 1H), 2.65 (m, 2H), 2.36 (m, 1H), 1.29 (s, 6H), 1.10 (d, 3H, J=6.63 Hz), 1.00 (t, 3H, J=6.63 Hz).

MP: 111-113° C.

MW: 493.62 g/mol; Molec. Form.: C$_{19}$H$_{27}$NO$_8$S$_3$.

Aqueous solubility (pH 5 phosphate buffer, 25° C.): 2900 µg/mL.

The invention claimed is:

1. A compound of the formula:

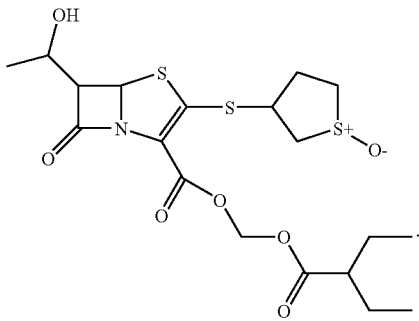

2. The compound of claim 1, which is (2-ethyl-1-oxobutoxy)methyl (5R,6S)-6-[(1R)-1-hydroxyethyl]-7-oxo-3-[[(1R,3S)-tetrahydro-1-oxido-3-thienyl]thio]-4-thia-1-azabicydo[3.2.0]hept-2-ene-2-carboxylate.

3. The compound of claim 1, which is (2-ethyl-1-oxobutoxy)methyl (5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylate in the crystalline form having an X-ray powder diffraction pattern substantially the same as that represented in FIGS. 3 and 5.

4. A pharmaceutical composition comprising the compound of claim 2 formulated for oral administration in admixture with one or more excipients.

5. A pharmaceutical composition comprising about 800 mg to about 2.5 g of the compound of claim 2, formulated for oral administration with one or more excipients.

6. A method of treating bacterial infection comprising orally administering a therapeutically effective amount of the compound of claim 2 to a human in need thereof.

7. A method of treating bacterial infection comprising orally administering a therapeutically effective amount of about 500 mg to about 2.5 g BID or TID of the compound of claim 2 to a human in need thereof.

8. A method of treating bacterial infection comprising orally administering a therapeutically effective amount of about 800 mg to about 1 g BID of the compound of claim 2 to a human in need thereof.

9. A method of treating bacterial infection comprising orally administering a therapeutically effective amount of about 7 mg/kg to about 25 mg/kg BID of the compound of claim 2 to a human in need thereof.

10. A method of treating bacterial infection comprising orally administering a therapeutically effective amount of about 17 mg/kg to about 45 mg/kg BID of the compound of claim 2 to a human in need thereof.

* * * * *